United States Patent [19]

Pelella et al.

[11] Patent Number: 5,764,656
[45] Date of Patent: Jun. 9, 1998

[54] METHOD FOR A FAST SCAN GRA CELL CIRCUIT

[75] Inventors: Antonio Raffaele Pelella, Highland Falls; Peter Tsung-shih Liu, Hopewell Junction; Gerard Joseph Scharff, Fishkill, all of N.Y.

[73] Assignee: International Business Machines Corporation, Armonk, N.Y.

[21] Appl. No.: 867,109

[22] Filed: Jun. 2, 1997

Related U.S. Application Data

[62] Division of Ser. No. 690,609, Jul. 31, 1996.

[51] Int. Cl.⁶ .................................................. G01R 31/28
[52] U.S. Cl. ................................ 371/22.31; 365/201
[58] Field of Search ........................ 371/22.31, 22.32, 371/22.36, 27.5, 27.6, 21.1; 365/189.01, 210, 154, 177, 230.05; 307/272.2, 475, 446, 465; 320/16, 40, 95

[56] References Cited

U.S. PATENT DOCUMENTS

| | | | |
|---|---|---|---|
| 5,488,614 | 1/1996 | Shima | 371/22.3 |
| 5,570,051 | 10/1996 | Chiang et al. | 327/203 |
| 5,606,526 | 2/1997 | Pilo | 365/189.05 |
| 5,612,632 | 3/1997 | Mahant-Shetti et al. | 326/46 |
| 5,633,606 | 5/1997 | Gaudet et al. | 327/202 |

OTHER PUBLICATIONS

Eckhardt et al., An high density 300 PS BICMOS GRA, IEEE 1992 Bipoar circuits and technology Meeting 8.3, pp. 178–181, Mar. 1992.

Petrovick et al., A 300K circuit ASIC logic family, 1990 IEEE international solid state circuits conference, pp. 88, 89, 270, Feb. 1990.

*Primary Examiner*—Robert Beausoliel, Jr.
*Assistant Examiner*—Nadeem Iqbal
*Attorney, Agent, or Firm*—Lynn L. Augspurger

[57] ABSTRACT

A GRA cell used in logic for digital systems has a master/slave latch circuit which has a L1 master latch circuit and an L2 slave latch circuit. The L1 master latch circuit having a first cross-coupled portion and a complementary write circuit coupled to the slave latch and having scan-in port coupled to pass a scan-in signal to an L1 pass gate NFET transistor. An A__Clock terminal port is connected to the L1 pass gate NFET transistor. The L2 slave latch's input is an output from the L1 master latch circuit. This L2 slave latch includes a second cross-coupled portion and a complementary write circuit. The L2 slave latch circuit is coupled to receive a signal resulting from the scan-in signal via said L1 latch circuit and an L2 pass gate NFET transistor for testing of said master/slave latch circuit. A B__Clock terminal is connected to the L2 pass gate NFET transistor. This allows testing to be used with the single NFET pass gate transistors for each latch. In order to reduce soft errors and required voltage and increase scan speed both L1 and L2 latch clock inputs during a scan function are connected respectively to their respective NFET pass gate transistors and to the source of their respective NFET feedback NFET transistor's circuit's source. During a test scan the pass gate and source of a feedback NFET transistor are coupled to their respective input clocks. The latch signal of each of said L1 master latch circuit and said L2 slave latch circuit receive their respective A__Clock and B__Clock signals, and turning each feedback NFET transistor fully on during one clock cycle and fully off during another portion of a clock cycle allows a very fast scan to be used during testing and diagnostic inspection of the circuit cell.

3 Claims, 2 Drawing Sheets

METHOD FOR A FAST SCAN GRA CELL CIRCUIT

RELATED APPLICATIONS

This application is a division of U.S. Ser. No. 08/690,609, filed Jul. 31, 1996.

FIELD OF THE INVENTION

This invention is related to a high speed logic circuits, and particularly to a method for a fast growable register array (GRA) which provides a fast scan with a first and a second pair of latches.

GLOSSARY OF TERMS

While dictionary meanings are also implied by certain terms used here, the following glossary of some terms may be useful.

FET Field Effect Transistor

GRA Growable Register Array as used in logic and in memory products and implemented in cell circuits.

BACKGROUND OF THE INVENTION

A latch circuit operates as a digital sample and hold circuit. It has two inputs, a data input and a clock. Information (true or complement) presented at the data input is transferred to the output when the clock goes high. When the clock goes low, the information that was present at the data input at the time the clock transition occurred is retained at the output. Thus, the trailing edge of the clock samples the data line and the circuit holds (stores) the binary information at the transition. Hence, this circuit is common in many digital circuits and widely used for many applications, particularly in random access memory (RAM) array design. A computer with RAM can perform both read and write operations. For each bit of storage, one flip-flop composed of a number of transistors, is used. Each flip-flop is composed of two cross-coupled gates, and this kind of memory is called a static memory. Thus a static RAM or SRAM stores a bit pattern in memory, and it is safe as long as power is on. Memories which use a capacitor to store data, store charges on the capacitance inherent in certain transistors, such as metal oxide semiconductor (MOS) transistors. These memories are dynamic and hence the term DRAM for dynamic random access memories.

Latches are used to receive data cell inputs and provide stored output. A classical approach to memory logic uses one latch L1 as a master latch and another cross coupled latch L2 as a slave latch. Latches are connected in series to form an array and separate clock signals (or inverted outputs of the same clock) are used as the clock for the L1 latch (A_CLOCK) and the L2 latch (B_CLOCK). Thus a series of L1 latches each will have RAM data inputs, an input line for write control operations of each RAM cell creates from the unique RAM input gated by logic from a Read/Write command, a RAM select and a RAM address decoder and this is all that is used in system mode.

The L2 latches don't bring any additional system functional features in system mode operations, but one L2 latch must be associated with each L1 latch as a slave to enable the array at each latch to be operated in a test mode, allowing for complete and automatic testing with a growable register array macro. Thus, for testing an L1 latch has a signal input and passes that signal to the slave L2 latch which provides a test or scan output in order to test the circuit. What is at the output of each latch is controlled by the clock transition of the L1 A_CLOCK and the L2 B_CLOCK. Latches are also used in circuits which don't provide for a growable register array (GRA) macro, and these are not GRA circuits when implemented as a logic cell.

As cells are composed of a group of transistors which form a function, a GRA memory cell will have some number of transistors. As our technology advances, it is desirable to make the cells as small as possible. Reducing the number of transistors is one way that has been approached. For instance, that number in a classical memory cell using L1 and L2 latches could require a minimum of 11 transistors. If the number of transistors could be reduced, that would save "real estate" and make more dense memory possible. However, function must be maintained. Lowering transistor numbers and size of elements reaches a minimum level and then the impact of many factors, the electrical effects of current flowing, of voltage, of soft errors makes further advances hard to obtain. A change in one element may have adverse and intolerable effects on another aspect of the cell. By review of art in the latch area, one will note that latches developed for one purpose are not suitable for another function or do not consider or satisfactorily solve aspects which should be considered as important.

U.S. Pat. No. 5,287,016 (assigned to International Business Machines Corporation, the assignee of the current application) describes a high-speed bipolar-field effect transistor (bi-fet) which includes a bipolar logic section which is clocked on and off by a first field effect transistor (FET) and a bipolar latch section which is clocked on and off by a second field effect transistor. This U.S. Pat. No. 5,287,016, does not deal with the speed of the latch itself, but is primarily related to latching the "output state" of a logic block in Bi-FET technology. The patent is not a GRA cell and concentrates on the integration of a latch into a logic block and switching between the "latch" mode and a "logic evaluation mode". We have determined that circuits which are common to general logic "cells", such as those employing latches and FETs could operate better.

Other patents illustrate various latch circuits with pass transistors and clock inputs which are not candidates for a GRA cell. For instance, the U.S. Pat. No. 4,493,077 relates to a Scan Testable Integrated Circuit and to controlling the scan operation of a traditional master/slave latch and is complex and not suitable as a cell candidate. This is not a GRA cell.

U.S. Pat. Nos. 4,855,699 and 5,155,432 don't show GRA cells, but relate to a System for Scan Testing of Logic Circuit Networks and also to master/slave latching circuits with multiple modes of operation. These patents show that the art teaches using a series of NFET transistors to isolate a latch feedback from a pass gate node. This means an additional transistor for each latch in order to break any latch feedback which is a disadvantage when one desires a fast design and also requires a separate clock to control its gate voltage.

U.S. Pat. No. 4,963,772 "Metastable-Immune FLip-Flop Arrangement" seems to be related to preventing noise from propagating for the master latch into the slave latch. Furthermore, the transistor technology is Bi-polar and the circuit family is ECL, so this patent is not a candidate for use in a small fast cell design for a GRA cell.

Another relatively flexible master/slave latching circuit which is not a GRA cell which supplies multiple modes of operation is that illustrated by U.S. Pat. No. 5,463,338 entitled "Dual Latch Clocked LSSD and Method". FIG. 3 of this patent shows a latch feedback isolated from the pass gate by a series NFET and PFET. These additional transistors are a problem in compact cell design.

While none of the above applications are GRA cells, there are a number of additional references which relate to GRA cells which have been reviewed.

A related patent, U.S. Pat. No. 5,465,060, issued Nov. 7, 1995 entitled "Fast Edge Triggered Self-Resetting CMOS Receiver with Parallel L1/L2 (Master/Slave) Latch" describes inventions of Antonio R. Pelella, an inventor herein. This patent shows generally a GRA SRAM cell which employs the circuit illustrated by FIG. 1 in its FIG. 5, but could benefit from our improvements illustrated by FIG. 2. This patent's disclosure is the same as U.S. Pat. No. 5,576,644, issued Nov. 19, 1996 from a divisional application Ser. No. 08/459,874, filed Jun. 2, 1995. For convenience in illustration the drawings of this application use corresponding reference numbers for elements of the latch shown in FIG. 5 of U.S. Pat. No. 5,465,060. This earlier patent is primarily related to receiving single ended data and generating a pulsing dual phase output signal suitable for a self-resetting CMOS environment. We note that this patent shows in FIG. 5 a latch feedback that is isolated from the pass gate node by a series of NFET and PFET, and we consider this prior art. These additional transistors are a problem in reaching greater densities in compact cell design and are eliminated in our invention.

Additionally, for applications of our invention, one can refer to other GRA implementations, such as Research Disclosure n310 02-90 of Aipperspach, AG, Schuelke, BA. This research disclosure described "Growable Register Array for High-Density CMOS Applications." in February, 1990. Described is a technique providing a high-density solution for small, single-port arrays and a variety of multi-port array applications. In the large-logic chip environment, storage element macros may require special circuit implementation to incorporate some form of an array self-test. The described technique saves much of the area that would normally be devoted to enhance testability of these designs. In FIG. 1 of this research disclosure, a Growable Register Array (GRA) consists of an array of shift register latches (SRLs) 10. The logic of the GRA is a common implementation. The WRITE address 20 gates the C-clock input to select the proper cell during a write operation. The outputs of SRLs 10 are passed to a Multiplexor (MUX) 30 which uses a READ address 40 to select the proper cell during a read access. By incorporating the MUX pass gate as part of the storage cell, significant layout advantages are attained. Because the storage elements are SRLs 10, full DC testability is possible. FIG. 2 of this research disclosure shows a simple representation of the basic design. Subsequent READ or WRITE ports are added by including the appropriate pass gates in the storage cell. Enhanced multiplexing is incorporated to increase the design's address space capabilities. Due to the structured nature of this technique, algorithmic generation of these circuits is easily accomplished, but this disclosure does not suggest the need for or provide for our improvements.

Our invention, while described in our preferred embodiment for complementary metal oxide semiconductor (CMOS) implementation, can also be employed in a bipolar-complementary metal oxide semiconductor (BiCMOS) GRA application. In a proceedings article entitled "A high density 300 ps BICMOS GRA" J. P. Eckhardt, S. G. Chu, and K. K Umino of IBM East Fishkill, Hopewell Junction, N.Y., USA., published in the IEEE, New York, N.Y., USA. Proceedings of the 1992 BIPOLAR/BiCMOS Circuits and Technology conference Meeting (Cat. No.92CH3177-3) 1992 P178-81, held in Minneapolis, Minn., USA 7-8 Oct., 1992, how a multiport BiCMOS embedded static RAM (SRAM) can be used as a growable register array (GRA) in high performance gate array technologies. This design provides read access times equivalent to those of bipolar RAMs, while maintaining soft error rates that are lower than those of CMOS. Read access times of 300 ps were achieved by eliminating all emitter coupled logic (ECL) to CMOS conversion from the read paths. Their then current implementation allowed array densities as high as 200 kb embedded in gate array logic. Our invention when employed in such applications would improve the scan speed in a BiCMOS implementation of a GRA latch cell, a need in all the discussed GRA prior developments.

Particularly fast growable register array (GRA) cells are needed which provide a fast scan with a compact cell design which has a pair of latches to enable dynamic testing of an array. We have tried to make a Growable Register Array (GRA) cell, which has a L1/L2 pair of latches and uses a single NFET pass gate to scan data into the L1 latch and L2 latch in order to reduce cell size. We find that a single NFET pass gate tends to scan slower and is more likely to fail at low voltages than a full pass gate pair (a NFET and PFET pass gate used in parallel). Therefore, when a single NFET pass gate has been used, it had trade-offs that are undesirable when used because of its smaller cell size needed for compact design. More dense memory products need more cells per area of a chip which carries the circuit, and more cells create heat which causes problems, and reducing voltage causes soft errors to occur with small cells, and so the design becomes difficult. Therefore, this past design gave up scan performance for cell size, and had problems in soft error rates, and in meeting functional voltage range criteria.

SUMMARY OF THE INVENTION

We have created a new compact cell design which is particularly suited to manufacture as a fast scan GRA cell with a master/slave or L1/L2 latching function during scanning. Our latch circuit has a clock input connecting the pass gate transistor and the source of a feedback NFET of each latch.

A feature of our fast scan GRA cell is that the clock inputs (A_Clock and B_Clock) that control the scan function are connected to the NFET pass transistor and the source of a single feedback NFET for each latch of the cell.

Our circuit allows the cell to have a faster scan performance compared with cells that do not have the clock inputs that control the scan function connected to the NFET pass transistor and the source of the feedback NFET of each latch of the cell.

A further achievement of the present invention is that it can function over a wider range of voltages, and it can provide for lower soft error rates by enabling the feedback transistors to be balanced (NFET/PFET strength ratio and sized to reduce soft error rates. This is particularly important in GRA cell applications which require low transistor counts in order to achieve the high density.

These and other improvements are set forth in the following detailed description. For a better understanding of the invention with advantages and features, refer to the description and to the drawings.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

DETAILED DESCRIPTION OF THE INVENTION

Before fully understanding our invention, the reader will need to refer to the latch circuit provided by the prior U.S. Pat. No. 5,465,060 and so we will first describe FIG. 1 which illustrates this prior undertaking in design which does not incorporate the invention described in our preferred embodiment illustrated by FIG. 2.

Figure 1:
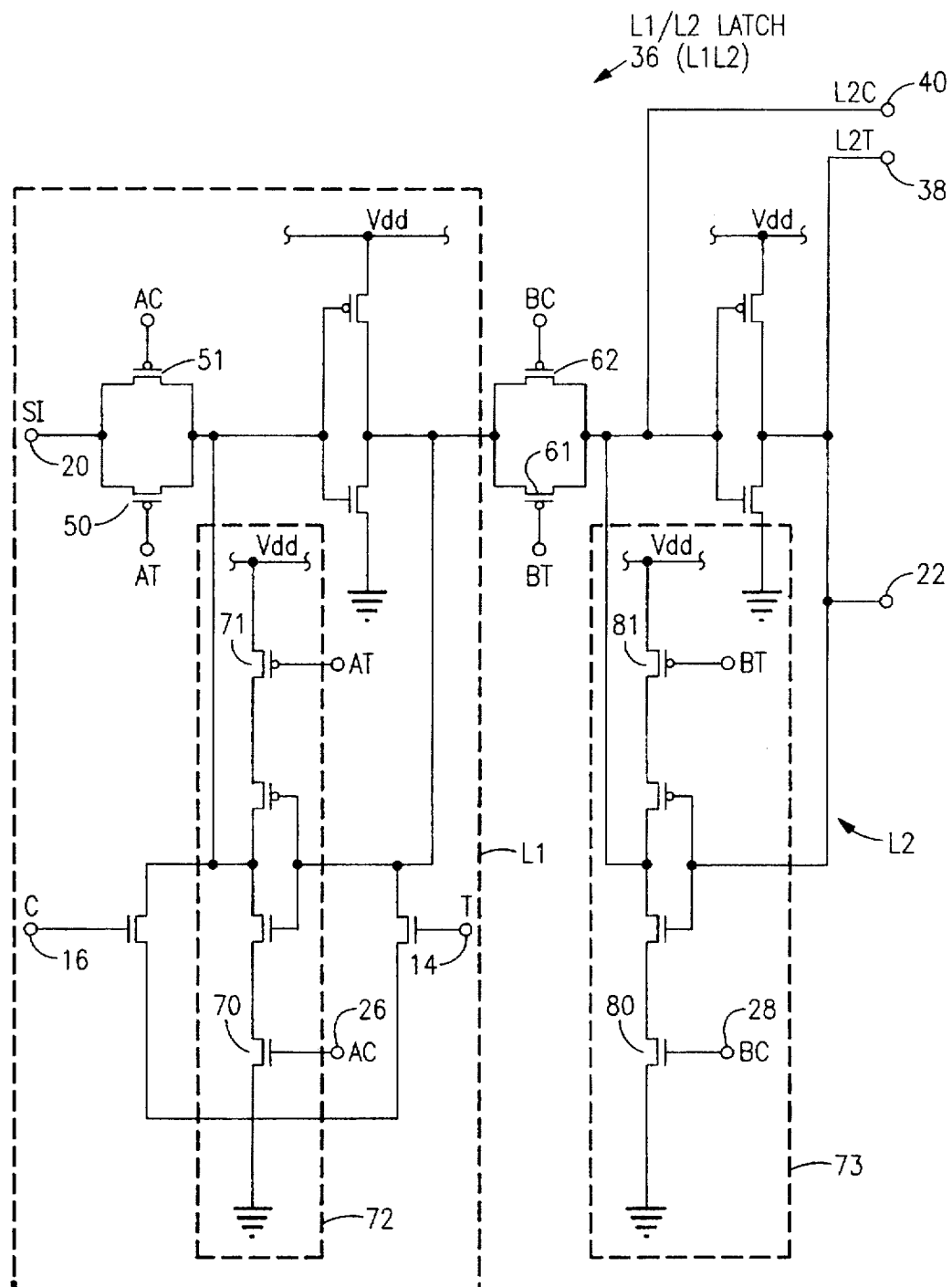
FIG. 1 is a schematic logic diagram of a GRA cell which does not incorporate our invention and which is PRIOR ART, corresponding to FIG. 5 of U.S. Pat. No. 5,465,060.

As illustrated by FIG. 1, growable register array (GRA) cells consist of a pair of latches, arranged in a master/slave relationship for receiving and latching data from a device such as a static random access memory (SRAM) or a dynamic random access memory (DRAM). Our preferred embodiment is used in an SRAM with CMOS technology, but as we will describe, it can be implemented in BiCMOS.

During the system mode of operation, the A & B scan clocks are inactive (signals at AT and BT are low, and AC and BC are high). Therefore, the L1 and L2 latches are holding data previously written into them. New data can be written into the L1 latch using the true (T) and complement (C) input signals 14 and 16, respectively, to reflect the current states of input (such as reflecting the output of a true complement generator). The contents of the L1 master set/reset latch (L1 in FIG. 1) may then be clocked by clock BC 28 (BT and BC are the L2 clocks in FIG. 1) into L2 Slave set/reset latch (L2) and feed other logic via a latch true L2T signal output line 38 and complement L2C signal output line 40. The latch circuit 36 (L1,L2) is a scannable latch having a scan-in port (SI) 20 and a scan out port 22. The scan-in port (SI) 20 is available for directly driving a test signal into L1 va the L1 pass gate (50 & 51). Similarly, an active B_CLOCK signal (BT & BC) at the L2 pass gate (61 & 62) can be clocked to scan data through the L2 latch allowing data to appear at the scan out port 22, useful for testing and diagnostic purposes. It should be noted that the feedback inverter 72 of latch L1 and the Feedback inverter 73 of latch L2 are grounded. Such a device has been useful in connection with the circuit illustrated by U.S. Pat. No. 4,465,060, issued Nov. 7, 1995 entitled "Fast Edge Triggered Self-Resetting CMOS Receiver with Parallel L1/L2 (Master/Slave) Latch" referenced above and shown therein as FIG. 5 of the U.S. patent.

Figure 2:
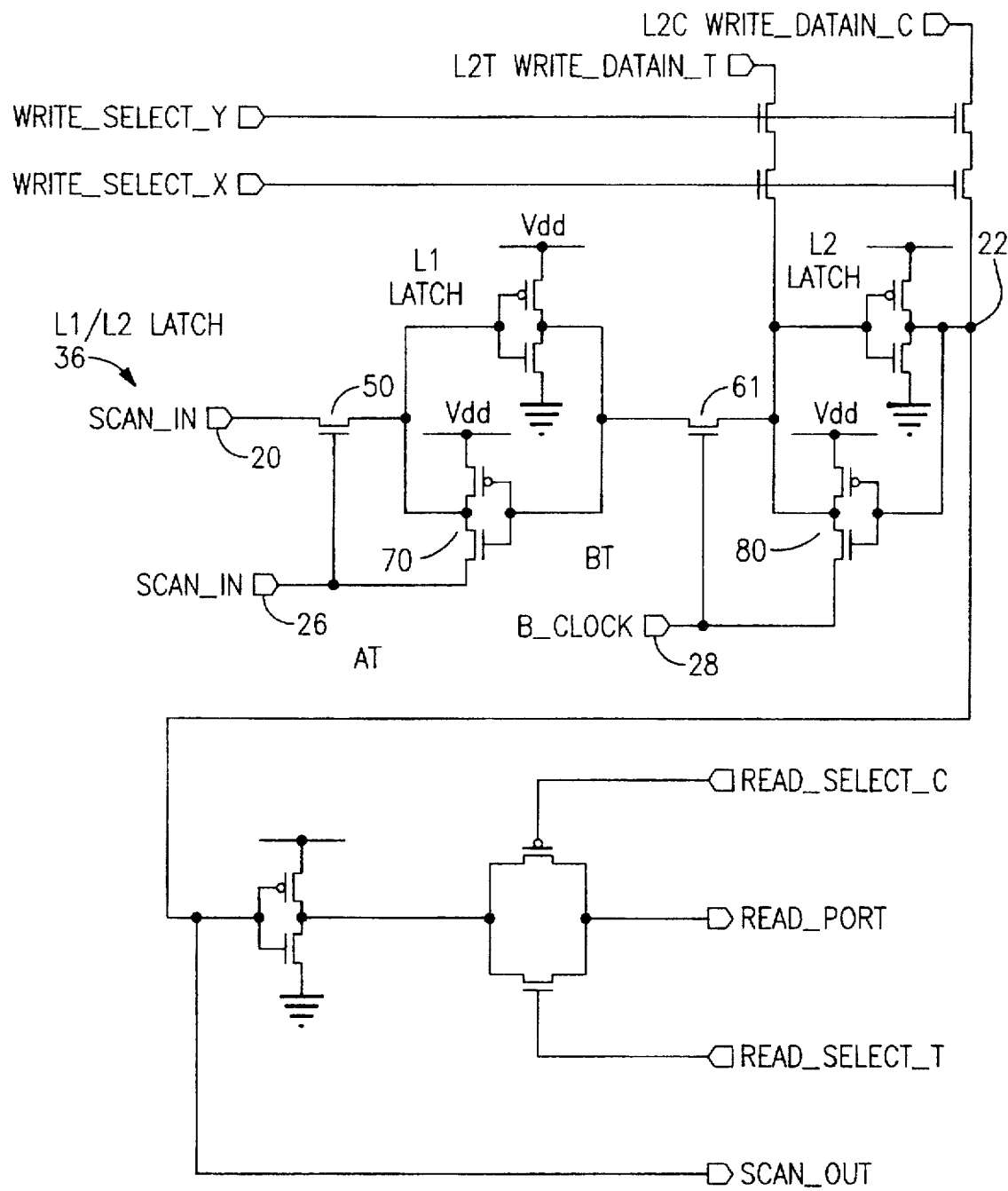
FIG. 2 is a schematic logic diagram of a GRA cell which is made and configured in accordance with our preferred embodiment.

Our improvement is illustrated in FIG. 2. As we have said, we have modified the circuit of FIG. 1 by providing in our preferred embodiment of our invention, illustrated for a SRAM cell, a cell with the clock input (AT and BT) of the L1 and L2 latch circuit connecting the pass gate transistor and the source of a feedback NFET of each latch.

Thus, our fast scan GRA cell has both the clock inputs (AT and BT) that control the scan function connected to the NFET pass transistor 50', 61' and the source of the feedback NFET (70', 80') each latch of the cell. The clock AC input which controls the cell scan function for L1 has its terminal connected to the L1 pass gate 50' NFET's gate, and to the source of the single feedback NFET 70' of the L1 latch. Similarly, the clock BT input which controls the cell scan function for L2 has its terminal connected to the L2 pass gate 61' NFET's gate, and to the source of the feedback 81' NFET of the L2 latch.

Here we note that the NFET and PFET transistors used to isolate the latch feedback from the pass gate node in FIG. 1, transistors 70, 71, 80 and 81 are additional transistors which are a problem in the cell design. Our new circuit illustrated by FIG. 2 enables elimination of these additional transistors 70, 71, 80 and 81.

This circuit arrangement achieved as shown in FIG. 2 not only effectively allows some reduction in real estate by eliminating transistors, but allows the cell to have a faster scan performance compared with cells that do not have the clock inputs that control the scan function connected to the NFET pass transistor and the source of the feedback NFET of each latch of the cell.

Our circuit change allows the current of the entire latch cell to be sinked through the clock. In order to achieve the fast scan, with the pass gate and source of the Feedback FET couples to the appropriate clock terminal, the Feedback FET is fully on during one clock cycle and fully off during another portion of the clock cycle. This further change in the circuit, by way of the operation of turning the Feedback FET is fully on during one clock cycle and fully off during another portion of the clock cycle is also of considerable importance.

With this change, Qcrit is increased, and further, one can increase the relative size of the latch to prevent soft errors from occurring from to minimal a size, even though the effective real estate size may be lower. Thus, our improved latch can function over a wider range of voltages, and it can provide for lower soft error rates by enabling a larger latch sizing, with still a reduction in real estate, while permitting the feedback transistors to be balanced (NFET/PFET strength ratio). As we have said, this is particularly important in GRA cell applications which require low transistor counts in order to achieve the high density.

It will be noted that our growable register array (CRA) cells, have eliminated a full pass gate pair. Cells which have a L1/L2 pair of latches with only a single NFET pass gate normally tend to scan slower and are more likely to fail, especially at low voltages. That is why some prior art examples used a NFET and PFET pass gate in parallel. However, the single NFET pass gate is preferable because of its smaller size. But, as we have indicated, in using such a cell a circuit designer must trade-off scan performance with cell size, and somehow avoid an unacceptable soft error rate, while achieving a reduced functional voltage range. With the use of our improved cell and its described operation, the prior undesirable trade-offs are avoided.

We disable the L1/L2 latch function during scanning. For example, during the scan into the L1 latch, the NFET feedback gate is disabled to break the latch. Notice that when AT is high, the NFET 51 turns off. This makes the L1 look like a simple inverter during the active scan clock (AT). When the scan clock (AT) goes inactive, the feedback is reactivated. This same technique is used for the L2 latch.

As illustrated by FIG. 2, growable register array (GRA) cells in accordance with our preferred embodiment comprises a pair of latches, arranged in a master/slave relationship. True (T) and complement (C) input signals 14' and 16' respectively, are directed to the L1/L2 latch by clock A 26' (AT is the L1 clock) to reflect the current states of input (such as reflecting the output of a true complement generator). The contents of the L1 master set/reset latch (L1 in FIG. 1) may then be clocked by clock B 28' (BC is the L2 clock in FIG. 1) into L2 slave set/reset latch (L2) and fed back to the input logic (the TCG) via a latch true LCT signal output line 38' and complement L2C signal output line 40'.

The latch circuit 36' (L1,L2) is a scannable latch having a scan-in port (SI) 20' and a scan out port 22'. The scan-in port (SI) 20' is available for directly driving a test signal into L1 via the L1 pass gate 51'. Similarly, a B_CLOCK test signal (BT) at the L2 Feedback Gate source 61' can be clocked through the L2 latch to appear at the scan out port 22' as is useful for testing and diagnostic purposes. It should be noted that the feedback gate source NFET 70' of latch L1 and the feedback gate source NFET 80' of latch L2 are both connected now to the respective input clocks (AT and BT).

Thus, with the "A" and "B" clocks now connected to the source of the feedback NFETS in both the L1 and L2 latches, the wiring changes allow use of a single NFET pass gate, eliminating the PFET used in parallel. This change allows faster scanning and the designer flexibility to lower the soft error rate by increasing the size of the L1/L2 Feedback transistors. The net result is a GRA cell that has a faster performance, and one which can function over a wider range of voltages with a lower soft error rate.

Such a device would also be useful in connection with the circuit illustrated by U.S. Pat. No. 5,465,060, issued Nov. 7, 1995 entitled "Fast Edge Triggered Self-Resetting CMOS Receiver with Parallel L1/L2 (Master/Slave) Latch" and it would thus provide the capability for a faster test scan.

Here we should recognize that our described invention employs in its preferred embodiment an L2 latch circuit separately clocked for the functional purpose of allowing a complete and automatic testing of the latch circuit. Thus, for operating our fast scan GRA cell circuit having a master/slave latch circuit which has a L1 master latch circuit and an L2 slave latch circuit. The L1 master latch circuit having a first cross-coupled portion and a complementary write circuit coupled to said slave latch and having scan-in port coupled to pass a scan-in signal to an L1 pass gate NFET transistor. In accordance with our invention an A_Clock terminal port is connected to the L1 pass gate NFET transistor. Our master feedback NFET transistor circuit has a source also coupled directly to the A_Clock terminal port.

Further, our a L2 slave latch's input is an output from the L1 master latch circuit. This L2 slave latch includes a second cross-coupled portion and a complementary write circuit as will be seen from FIG. 2. The L2 slave latch circuit is coupled to receive a signal resulting from the scan-in signal via said L1 latch circuit and an L2 pass gate NFET transistor for testing of said master/slave latch circuit. A B_Clock terminal is connected to the L2 pass gate NFET transistor, and we have also provided a slave feedback NFET transistor circuit having a source also coupled directly to said B_Clock terminal port. This allows a testing function to be used with the single NFET pass gate transistors for each latch. Both clock inputs during a scan function are connected respectively to their respective NFET pass gate transistors and to the source of their respective NFET feedback NFET transistor's circuit's source. During a test scan the pass gate and source of a feedback NFET transistor are coupled to their respective input clocks. The latch signal of each of said L1 master latch circuit and said L2 slave latch circuit receive their respective A_Clock and B_Clock signals, and turning each feedback NFET transistor fully on during one clock cycle and fully off during another portion of a clock cycle allows a very fast scan to be used during testing and diagnostic inspection of the circuit cell.

The reader reviewing FIG. 2 will note the usual additional input and output circuitry to our improved latch for handling the write select, and write data, inputs and the read select and read data outputs. These are complementary to our invention.

While we have described our preferred embodiments of our invention, it will be understood that those skilled in the art, both now and in the future, may make various improvements and enhancements which fall within the scope of the claims which follow. These claims should be construed to maintain the proper protection for the invention first disclosed.

What is claimed is:

1. A method of operating a fast scan GRA cell circuit having a master/slave latch circuit having a L1 master latch circuit and an L2 slave latch circuit, said L1 master latch circuit having a first cross-coupled portion and a complementary write circuit coupled to said slave latch and having scan-in port coupled to pass a scan-in signal to an L1 pass gate NFET transistor, an A_Clock terminal port connected to said L1 pass gate NFET transistor, and a master feedback NFET transistor circuit having a source also coupled directly to said A_Clock terminal port, and further having a L2 slave latch whose input is an output from said master latch circuit, said L2 slave latch including a second cross-coupled portion and a complementary write circuit, said L2 slave latch circuit being coupled to receive signal resulting from said scan-in signal via said L1 latch circuit and an L2 pass gate NFET transistor for testing of said master/slave latch circuit, a B_Clock terminal connected to said L2 pass gate NFET transistor, and a slave feedback NFET transistor circuit having a source also coupled directly to said B_Clock terminal port, whereby both clock inputs during a scan function are connected respectively to their respective NFET pass gate transistors and to the source of their respective NFET feedback NFET transistor's circuit's source, and wherein said method includes during a scan coupling the pass gate and source of a feedback NFET transistor latch signal of each of said L1 master latch circuit and said L2 slave latch circuit to receive their respective A_Clock and B_Clock signals, and turning each feedback NFET transistor fully on during one clock cycle and fully off during another portion of a clock cycle.

2. A method of operating a fast scan GRA cell circuit according to claim 1 wherein during scanning the L1/L2 latch function is disabled.

3. A method of operating a fast scan GRA cell circuit according to claim 2 wherein during the scan into the L1 latch, the NFET feedback gate for said L1 master latch circuit is disabled to break the latch to make the L1 master latch circuit function as a simple inverter during an active scan clock, and, when active scan clock goes inactive, the feedback is reactivated, and said during the scan the NFET feedback gate for said L2 slave latch circuit is disabled to break the latch to make the L2 slave latch circuit function as a simple inverter during an active scan clock, and, when active scan clock goes inactive, the feedback for said L2 slave latch circuit is reactivated.

* * * * *